United States Patent [19]

Benjamin et al.

[11] Patent Number: 5,071,577

[45] Date of Patent: Dec. 10, 1991

[54] PHOSPHITE DERIVED PROPYLENE BASED MULTIFUNCTIONAL LUBRICANTS AND MULTIFUNCTIONAL LUBRICANT ADDITIVES

[75] Inventors: Linda A. Benjamin, Horsham, Pa.; Andrew G. Horodysky, Cherry Hill, N.J.; Derek A. Law; Nancy M. Page, both of Yardley, Pa.

[73] Assignee: Mobil Oil Corporation, Fairfax, Va.

[21] Appl. No.: 292,054

[22] Filed: Dec. 30, 1988

[51] Int. Cl.⁵ .................... C10M 1/46; C10M 105/74
[52] U.S. Cl. .................... 252/46.6; 252/32.5; 252/49.8; 252/49.9; 525/340; 558/81; 558/85; 558/119; 558/166; 558/179; 558/183; 558/190; 558/198; 558/214
[58] Field of Search ............ 252/32.5, 46.6, 49.8, 252/49.9; 525/340; 585/332; 558/85, 119, 81, 179, 183, 166, 190, 198, 214

[56] References Cited

U.S. PATENT DOCUMENTS

| | | | |
|---|---|---|---|
| 2,759,010 | 8/1956 | Lorenzo et al. | 260/461 |
| 2,826,620 | 3/1958 | Matuszaka | 585/332 |
| 2,839,563 | 7/1958 | Hechenbleikner | 44/63 |
| 2,863,834 | 12/1958 | Buckmann | 525/340 |
| 3,014,956 | 12/1961 | Birum | 44/63 |
| 3,281,356 | 10/1966 | Coleman | 252/32.7 E |
| 3,290,276 | 12/1966 | Anderson | 252/49.8 |
| 3,350,348 | 10/1967 | Braid et al. | 252/46.6 |
| 3,440,247 | 4/1969 | Dorer, Jr. | 44/63 |
| 3,544,465 | 12/1970 | Braid | 252/46.6 |
| 3,574,795 | 4/1971 | Oswald et al. | 260/956 |
| 3,584,082 | 6/1971 | Korpics et al. | 252/49.8 |
| 3,644,206 | 2/1972 | Braid | 252/46.7 |
| 3,972,243 | 8/1976 | Driscoll et al. | 252/49.8 |
| 4,212,753 | 7/1980 | Horodysky | 252/46.6 |
| 4,532,057 | 7/1985 | Horodysky et al. | 252/49.8 |
| 4,557,845 | 12/1985 | Horodysky et al. | 252/49.9 |
| 4,704,218 | 11/1987 | Horodysky et al. | 252/46.6 |
| 4,705,879 | 11/1987 | Dressler | 252/49.8 |
| 4,752,416 | 6/1988 | Scharf et al. | 252/49.8 |
| 4,870,038 | 9/1989 | Page et al. | 502/62 |

FOREIGN PATENT DOCUMENTS 1440129 11/1972 United Kingdom .

*Primary Examiner*—Margaret B. Medley
*Attorney, Agent, or Firm*—Alexander J. McKillop; Charles J. Speciale; Howard M. Flournoy

[57] ABSTRACT

Novel phosphite derivatives of propylene based lube olefins are novel lubricating fluid media with internal synergistic multifunctional extreme pressure, antiwear and antioxidant properties. These compounds exhibit the same multifunctional characteristics when used in minor additive amounts in either mineral or synthetic lubricating oils as well as fuels.

34 Claims, No Drawings

PHOSPHITE DERIVED PROPYLENE BASED MULTIFUNCTIONAL LUBRICANTS AND MULTIFUNCTIONAL LUBRICANT ADDITIVES

CROSS-REFERENCE TO RELATED APPLICATIONS

This application is related to Ser. No. 07/292,039, Mobil docket number 5138, which issued as U.S. Pat. No. 5,006,271 on Apr. 9, 1991;

This application is related to Ser. No. 07/292,079, Mobil docket number 5030, now pending;

This application is related to Ser. No. 07/292,080, Mobil docket number 5122, which issued as U.S. Pat. No. 4,983,310 on Jan. 8, 1991;

This application is related to Ser. No. 07/685,968, Mobil docket number 5107FC, now pending.

BACKGROUND OF THE INVENTION

This invention relates to the preparation of novel organophosphorus compounds. More particularly, this invention relates to the preparation of phosphonate adducts of propylene based lube-range olefins. The products obtained from the reaction of a propylene based lube olefin and various functionalized phosphites are unique in composition, structure and utility.

The use of metallic phosphorodithioate derivatives, such as zinc dithiophosphates, has been well-known for their multifunctional antioxidant/antiwear/anticorrosion properties in a variety of lubricant applications, especially in engine oils.

The use of ashless phosphorodithioate derivatives, such as alkylmercapto-alkyl-O,O-dialkyldithiophosphates (U.S. Pat. No. 2,759,010), phosphorodithioate esters (U.S. Pat. Nos. 3,544,465, 3,350,348 and 3,644,206), reaction products of sulfurized olefin adducts of phosphorodithioic acids (U.S. Pat. No. 4,212,753), and addition products of dihydrocarbyl thiophosphoric acids to conjugated dienes (U.S. Pat. No. 3,574,795), have found widespread use in a variety of lubricant applications as multifunctional anticorrosion, antiwear, and antioxidant additives, as well as in agriculture applications as herbicides and pesticides.

Lubricants, such as lubricating oils and greases, are subject to oxidative deterioration at elevated temperatures or upon prolonged exposure to the elements. Such deterioration is evidenced, in many instances, by an increase in acidity and in viscosity, and when the deterioration is severe enough, it can cause metal parts to corrode. Additionally, severe oxidation leads to a loss of lubrication properties, and in especially severe cases this may cause complete breakdown of the device being lubricated. Many additives have been tried, however, many of them are only marginally effective except at high concentrations. Improved performance is clearly needed.

Water (moisture) is another critical problem. In spite of even extraordinary precautionary efforts water is found as a film or in minute droplets in vessels containing various hydrocarbon distillates. This brings about ideal conditions for corrosion and damage of metal surfaces of the vessels and the materials contained therein. Also in the lubrication of internal combustion engines, for example, quantities of water are often present as a separate phase within the lubricating system. Another serious problem in respect to metallic surfaces in contact with adjacent metallic surfaces is the surface wear caused by the contact of such surfaces. One material capable of effectively coping with such problems as these simultaneously, is highly desirous.

The peroxide catalyzed reaction of dialkyl hydrogen phosphites with conventional olefins to give phosphonate derivatives is known as disclosed in U.S. Pat. No. 2,957,931. It has also been disclosed in U.S. Pat. Nos. 3,340,332 and 3,483,278 that O,O-dihydrocarbyl dithiophosphoric and monothiophosphoric acids add to olefinic compounds, i.e. monoolefins, multiolefins and conjugated diolefins in the presence of free radical initiators. In all of these patents, typical free radical initiators include ultraviolet light, gamma irradiation on chemical free-radical initiators such as peroxides, etc.

The reaction products in accordance with this invention are, however, novel lubricating fluids as well as novel additives. The incorporation of the herein disclosed phosphite derivatives onto the backbone of the propylene based lube olefin provides the basis for the unique internal synergistic extreme pressure/antiwear activity, thermal stability and lubricity. These phenomena are equally advantageous when these compositions are used at 100%, less than 100% or 10–90 wt. % partial fluid replacement levels or at 0–10 wt. % additive concentrations.

Accordingly, it is an object of this invention to provide lubricant compositions and fuel compositions having improved multifunctional capability comprising antioxidant/high temperature stabilizing properties, antiwear/EP activity with corrosion-inhibiting and friction-reducing characteristics. It is a further object to provide novel additive properties derived from the aforementioned phosphite derived adducts of propylene based olefins to such compositions.

SUMMARY OF THE INVENTION

This application is directed to reaction products of propylene based lube (PBL) olefins with various functionalized phosphites which exhibit excellent lubricating properties in conjunction with good extreme pressure/antiwear, antioxidant and friction reducing properties. Different types of derivatives may be prepared by reacting different phosphites with the lube olefin, thereby providing a variety of derivatives which have particular utility in a variety of applications.

These titled compounds can also function as functionalized fluids. They may be used in a number of organic fluids to impart extreme pressure/antiwear, antioxidant or friction reducing properties thereto. Primarily, these additives are used in lubricating oils, such as petroleum mineral oils and synthetic hydrocarbon oils. Additionally, hydrocarbon fuels, such as the petroleum based fuels, i.e. gasoline, kerosene and heavier fuel oils, may require extreme pressure/antiwear activity, thermal stability and/or frictional protection.

The functionalized compositions, as described in this patent application, as lubrication fluids and additives in either a mineral or synthetic lubricant are novel and unique and provide unprecendented performance benefits due to inherent internal synergism. The process of enhancement of the lubricating properties via the addition of these compositions to either mineral or synthetic lubricants is also believed novel and to be unique. Post-reactions of these unique functionalized phosphite-lube olefin adducts with small amounts of functionalized olefins such as vinyl esters, vinyl ethers, acrylates and methacrylates are also believed to be novel.

DESCRIPTION OF PREFERRED EMBODIMENTS

It has now been found that the incorporation of functionalized phosphites onto the backbone of lube olefins in accordance herewith offers unique advantages over conventional olefins where volatility, extraction or thermal stability is considered to be important. The propylene based lube olefins are themselves unique in that traditional high-quality high viscosity index lube olefins are generally prepared from 1-decene, not propylene. The products from the reaction of novel functionalized phosphites with propylene based lube olefin oligomers are unique and not evident in any prior art known to applicants.

The propylene based lube olefins were prepared (as more fully disclosed in Ser. No. 140,361 filed Jan. 4, 1988 and now U.S. Pat. No. 4,870,038) in the following manner: propylene was oligomerized over a 2,4,6-collidine modified HZSM-23 zeolite catalyst. The product consisting of $C_6$–$C_{30}$ olefins was distilled and the $\geq C_{12}+$ fraction was oligomerized over HZSM-5 zeolite catalyst. This product was distilled to give the resultant lube olefin.

Approximately 80% to 95% of this material had a boiling point greater than or equal to 700° F. with about 70% of the total mixture having a boiling point greater than or equal to 750° F. These materials typically have VI's in the range of 80 to 125 and more preferably 100 to 115 with kinematic viscosity (100° C.) of about 4 to 7 cs. and more preferably 5.0 to 5.5 cs. The PBL olefin oligomers have a molecular weight average of about 350 to about 4000 and preferably 400 to about 2000.

Propylene-based lube (PBL) olefin derived adducts of aliphatic vicinal diol derived phosphites (I) possess unexpected antiwear properties and exhibit friction reduction, enhanced hydrolytic stability and additive solubilizing features from the vicinal diol group. Analogous sulfide-containing vicinal fluid derived phosphite (II) lube olefin adducts provide better antioxidant/antiwear properties. These effects are synergistic due to both the sulfur and the phosphorus incorporation. Similarly, ether alcohol derived phosphite (III) adducts of PBL olefins provide improved chelating ability and solubility/detergency with the ether linkage. Amino alcohol derived phosphite (IV) adducts improve rust inhibition and emulsibility/demulsibility properties. Hydroxyester derived phosphite (V) adducts improve frictional properties, rust inhibiting characteristics and additive solubility in the PBL base fluid. Some heterocyclic substituted alcohol derivatives. e.g. imidazolines (VI) and oxazolines (VII), exhibit antirust, friction reducing and dispersant type properties. Alkoxylated amine phosphite adducts (VIII) improve friction reducing and antiwear performance in addition to rust inhibition. Phosphorodithioate (IX) derived adducts are multidimensional in that the phosphorus/sulfur moiety provides antioxidant/antiwear properties, the other linkage provides solubility characteristics while the phosphite end provides enhanced EP/antiwear properties. Aromatic derived phosphites, e.g. catechol (X), resorcinol, phenolic or substituted catechol, resorcinol, phenolic, all contain an intrinsic synergistically placed antioxidant group which may be released under hydrolytic conditions or otherwise in service conditions. In addition, these multifaceted phosphite adducts exhibit antiwear properties and friction modifying properties.

All of the above mentioned propylene-based lube olefin-phosphite adducts exhibit beneficial properties from the unique olefin in combination with those properties unique to a given functionalized phosphite, and it is believed that this combination provides for a novel structural class and a unique multifaceted synergistic set of properties. The use of these compositions of matter to improve the above lubricant features either as a functional fluid or partial fluid replacement or as additives for lubricants is therefore, believed to be novel.

Selected Multifunctional Phosphorus Containing Moieties

(I)

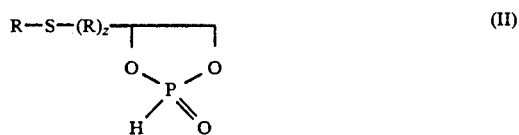

(II)

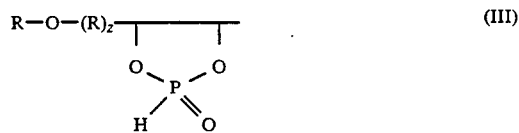

(III)

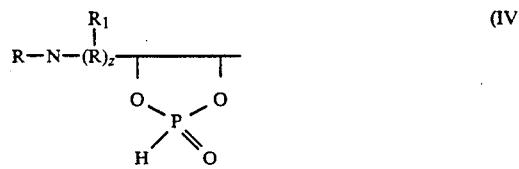

(IV)

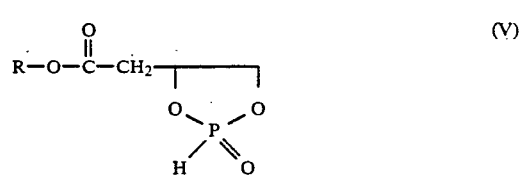

(V)

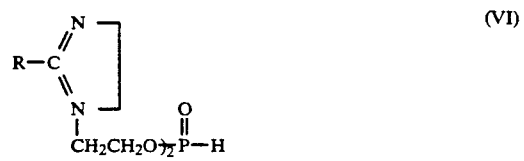

(VI)

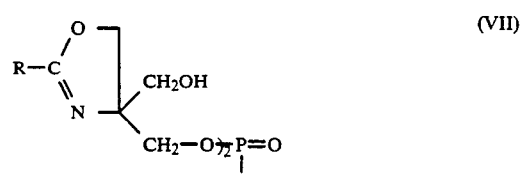

(VII)

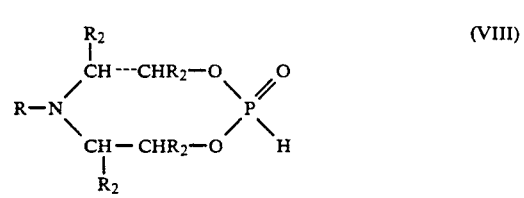

(VIII)

-continued

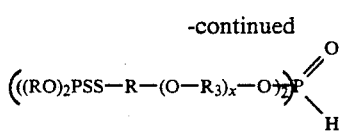
(IX)

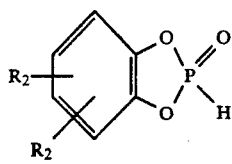
(X)

Open chain derivatives and/or oligomeric derivatives of I–V, VIII and X, and cyclic derivatives of VII can also be used. Esters related to structure V, including phosphites of trimethylol propane monooleate, petanerythritol oleate, and the like can also be used.

Where R is a carbon radical of an aliphatic or aromatic moiety, substituted or unsubstituted, linear, cyclic or heterocyclic and, can optionaly contain sulfur, oxygen, and/or nitrogen or mixtures thereof.

Where $R_1$ is hydrogen or a $C_1$ to about a $C_{18}$ carbon radical of an aliphatic moiety, linear or branched, and optionally contains S, N, and/or O or mixtures thereof.

Where $R_2$ is hydrogen or a $C_1$ to about a $C_{18}$ aliphatic carbon radical either linear or branched, and can additionally contain S, N, and O.

Where $R_3$ is an aliphatic carbon radical of at least $C_2$ carbon to about $C_{18}$, Where Z is 0 or 1 and X is 1 through 10.

More conventional type phosphites or phosphite esters can also provide a final product with improved antiwear and/or friction reducing properties. For example, reaction products of PBL olefin with a hydrogen phosphite of the following formula yield lube adducts with improved properties.

Where R' and R" are independently alkyl of 1 to 18 carbon atoms, cycloalkyl of 2 to 12 carbon atoms, phenyl, phenyl substituted by alkyl of 1 to 18 carbon atoms, aralkyl of 7 to 9 carbon atoms. R' and R" may also be derived from alcohols other than hydrocarbons, e.g. ether alcohols, amino alcohols, sulfur-containing alcohols and diol type alcohols. The hydrogen phosphite may additionally be of the following formula.

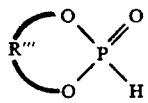

Where R''' is an alkyl or alkenyl group of 2 to 12 carbon atoms, phenyl, phenyl substituted by alkyl of 1 to 18 carbon atoms, aralkyl and substituted aralkyl derivatives and, optionally additives containing sulfur, nitrogen and oxygen.

Generally speaking in preparation of the various reactants, reaction times, temperatures, pressures and quantities utilized may vary widely and are not believed to be critical. However, reaction temperatures usually vary from about 80° to about 250° C. at ambient or higher pressures if so desired for a period of time of two up to 12 hours or more and in molar ratios varying from less than molar to substantially equimolar to more than molar or from about 1:1 to about 1:2–10 moles of olefin to phosphite.

The reaction products may be incorporated in additive quantities into any suitable lubricating media comprising oils of lubricating viscosity or greases or other solid lubricants prepared therefrom or also into liquid hydrocarbon fuels. The fuels contemplated herein include gasolines, alcohols, gasohol, distillates diesel fuels and/or mixtures thereof. When used as an additive products of this invention are useful in the above mentioned media in concentrations of from about 0.001 to 10 wt. %, preferably from about 0.1 to 1.0 wt. %. However, when used in fuel compositions preferably they are useful in amounts of from about 25 to 100 lbs. per 1000 barrels of fuel.

Fully formulated lubricating oils may include a variety of additives (for their known purpose) such as dispersants, detergents, inhibitors, antiwear agents, antioxidant, antifoam, pour depressant and other additives including phenates, sulfonates and zinc dithiophosphates. As hereinbefore indicated, the aforementioned additive compounds may be incorporated as multifunctional agents in grease compositions. When high temperature stability is not a requirement of the finished grease, mineral oils having a viscosity of at least 40 SSU at 150° F., and particularly those falling within the range from about 60 SSU to about 6,000 SSU at 100° F. may be employed. The lubricating vehicles of the improved greases of the present invention, containing the above described additives, are combined with a grease forming quantity of a thickening agent. For this purpose, a wide variety of materials dispersed in the lubricating vehicle in grease-forming quantities in such degree as to impart to the resulting grease composition the desired consistency. Exemplary of the thickening agents that may be employed in the grease formulation are non-soap thickeners, such as surface-modified clays and silicas, aryl ureas, calcium complexes and similar materials. In general, grease thickeners may be employed which do not melt and dissolve when used at the required temperature within a particular environment; soap thickeners such as metallic (lithium or calcium) soaps including hydroxy stearate and/or stearate soaps can be used however, in all other respects, any material which is normally employed for thickening or gelling hydrocarbon fluids or forming greases can be used in preparing the aforementioned improved greases in accordance with the present invention.

Included among the preferred thickening agents are those containing at least a portion of alkali metal, alkaline earth metal or amine soaps of hydroxyl-containing fatty acids, fatty glycerides and fatty esters having from 12 to about 30 carbon atoms per molecule. The metals are typified by sodium, lithium, calcium and barium. Preferred is lithium. Preferred members among these acids and fatty materials are 12-hydroxystearic acid and glycerides containing 12-hydroxystearates, 14-hydroxystearic acid, 16-hydroxystearic acid and 6-hydroxystearic acid.

Other thickening agents include salt and salt-soap complexes as calcium stearate-acetate (U.S. Pat. No. 2,197,263), barium stearate acetate (U.S. Pat. No. 2,564,561), calcium, stearate-caprylate-acetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

Additionally, the combination of lubricant formulations containing the above compositions may be used with any of the following supplemental additives: dispersants, detergents, viscosity index improvers, EP/antiwear additives, antioxidants, pour depressants, emulsifiers, demulsifiers, corrosion inhibitors, antirust inhibitors, antistaining additives, friction modifiers and the like and also are believed to be novel.

As mentioned hereinabove these lubricating additive compositions may be used in amounts up to 100% to provide the lubricating media in its entirety. Thus, the adducts described herein may be used in amounts up to 100%, e.g., 50 to 100% to provide a complete lubricating media but may be used in amounts less than 100% e.g., from 10–90% as partial replacement fluids in addition to their above-mentioned use as additive products.

The following examples are exemplary and are not intended to be limitations on the scope of this invention.

EXAMPLE 1

To 15 g (0.04 mole) of a propylene based lube olefin at 160° C. under a nitrogen sparge was added dropwise over a 0.5 hour period 3.67 grams (0.02 mole) of dibutyl hydrogen phosphite and 0.03 wt % di-tert-butyl peroxide. The reaction mixture was stirred for 2 hour at 160° C. The reaction mixture was distilled under vacuum to remove tert-butanol and unreacted phosphite. The resulting product was filtered through diatomaceous clay to yield a light yellow oil (16.74 grams). The product had the following elemental analysis:

% P=3.16.

EXAMPLE 2

The procedure of Example 1 was repeated using 15 grams (0.04 mole) of a propylene based lube olefin, 0.73 grams (0.004 mole) of dibutyl hydrogen phosphite and 0.03 wt % di-tert-butyl peroxide. The product was a clear yellow-orange oil (14.20 grams) and had the following elemental analysis:

% P=0.85.

EVALUATION OF PRODUCTS

The products of the above examples were evaluated as functional fluids. The results were compared to fully formulated test mineral oil as well as the underivatized lube olefin. These data were obtained on the Four-Ball Wear Apparatus (Test Method D 2266, Tables 1 and 2) (2000 rpm, 200° F., 60 kg).

TABLE 1

|  | Wear Scar (mm) |
|---|---|
| Test Oil (fully formulated automatic engine oil containing detergent/disperant inhibiting package) | 3.79 |
| PBL Olefin | 5.22 |
| Example 1 | 0.48 |
| Example 2 | 0.82 |

The products of the above examples were also evaluated at 1 wt % concentration in a standard test mineral oil. The results were compared to the test oil without additive. These data were obtained on the Four-Ball Wear Apparatus (2000 rpm, 200° F., 60 kg).

TABLE 2

|  | Additive Concentration, wt % | Wear Scar (mm) |
|---|---|---|
| Test Oil (80%/20% mixture of solvent paraffinic bright/solvent paraffinic neutral lubricating oil) | 0 | 3.79 |
| PBL Olefin | 1 | 4.51 |
| Example 1 | 0 | 0.66 |
| Example 2 | 1 | 0.56 |

The coupling of unique propylene based lube olefins with the non-traditional multifunctional phosphite derivatives described in this patent application leads to novel lubricants and lubricant additives. These compositions have enhanced oxidative stability, reduced wear, impoved rust inhibition and increased load carrying capabilities. These unique adducts have widespread application as an additive in mineral or synthetic base stocks.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

We claim:

1. A lubricant composition comprising a major amount of an oil of lubricating viscosity or grease or other solid lubricant prepared therefrom and a minor multifunctional amount of the reaction product of a propylene based lube olefin oligomer and a functionalized phosphite selected from the group consisting of vicinal diol derived phosphites, sulfide containing vicinal derived phosphites, ether alcohol derived phosphites, amino alcohol derived phosphites, hydroxy-ester derived phosphites, heterocyclic substituted alcohol derived phosphites, alkoxylated amine phosphites, phosphorodithioate derived phosphites and aromatic derived phosphites or open chain and oligomeric derivatives thereof having a functionalized carbon radical of an aliphatic or aromatic moiety substituted or unsubstituted, linear or branched and optionally containing sulfur, oxygen and/or nitrogen or mixtures thereof, wherein the reaction temperature varies from about 80° to 250° C. under ambient or slightly higher pressures or autogenous pressures and the molar ratio of propylene base lube olefinic oligomer to phosphite varies from less than molar, more than molar or equimolar amounts and wherein the propylene based lube olefin oligomer has a kinematic viscosity at 100° C. of about 4 to 7 cs. and a VI in the range of 80 to 125), about 80 to 95% of which boils at about 700° F. and about 70% of said propylene based lube olefin has a BP≧750° F.

2. The composition of claim 1 wherein said PBL olefin has a kinematic viscosity at 100° C. of about 5.5, and a VI in the range of 100 to 115.

3. The composition of claim 1 wherein said phosphite has the following generalized structure:

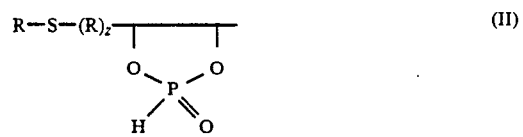

(II)

or open chain and/or oligomeric derivative thereof
where R is a functionalized carbon radical of an aliphatic or aromatic moiety, substituted or unsubstituted, linear or branched and optionally contains sulfur, oxygen, and/or nitrogen or mixtures thereof,
where z is 1.

4. The composition of claim 1 wherein said phosphite has the following generalized structure:

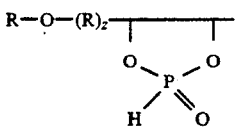
(III)

or open chain and/or oligomeric derivative thereof
where R is a functionalized carbon radical of an aliphatic or aromatic moiety, substituted or unsubstituted, linear or branched and optionally contains sulfur, oxygen, and/or nitrogen or mixtures thereof,
where z is 1.

5. The composition of claim 1 wherein said phosphite has the following generalized structure:

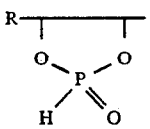
(I)

or open chain and/or oligomeric derivatives thereof where R is a functionalized carbon radical of an aliphatic or aromatic moiety substituted or unsubstituted, linear or branched and optionally containing sulfur, oxygen and/or nitrogen or mixtures thereof.

6. The composition of claim 1 wherein said phosphite has the following generalized structure:

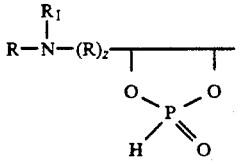
(IV)

or open chain and/or oligomeric derivative thereof
where R is a functionalized carbon radical of an aliphatic or aromatic moiety, substituted or unsubstituted, linear or branched and optionally contains sulfur, oxygen, and/or nitrogen or mixtures thereof,
where $R_1$ is hydrogen or a functionalized $C_1$ to about a $C_{18}$ carbon radical of an aliphatic moiety, linear or branched, optionally containing sulfur, nitrogen, and/or oxygen or mixtures thereof,
where Z is 1.

7. The composition of claim 1 wherein said phosphite has the following generalized structure:

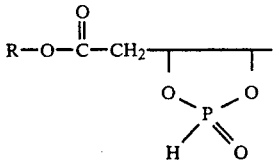
(V)

or open chain and/or oligomeric derivative thereof
where R is a functionalized carbon radical of an aliphatic or aromatic moiety, substituted or unsubstituted, linear or branched and optionally containing sulfur, oxygen, and/or nitrogen or mixtures thereof.

8. The composition of claim 1 wherein said phosphite has the following generalized structure or open chain:

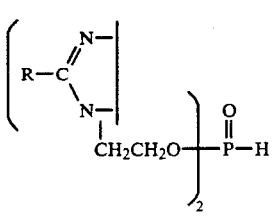
(VI)

where R is a functionalized carbon radical of an aliphatic or aromatic moiety, substituted or unsubstituted, linear or branched and optionally containing sulfur, oxygen, and/or nitrogen or mixtures thereof.

9. The composition of claim 1 wherein said phosphite has the following generalized structure:

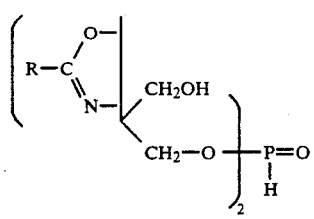
(VII)

or cyclic derivative thereof
where R is a functionalized carbon radical of an aliphatic or aromatic moiety, substituted or unsubstituted, linear or branched and optionally containing sulfur, oxygen, and/or nitrogen or mixtures thereof.

10. The composition of claim 1 wherein said phosphite has the following generalized structure:

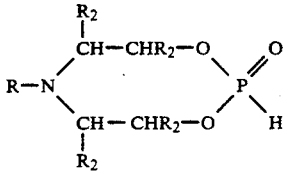
(VIII)

or open chain and/or oligomeric derivative thereof
where R is a functionalized carbon radical of an aliphatic or aromatic moiety, substituted or unsubstituted, linear or branched and optionally containing sulfur, oxygen, and/or nitrogen or mixtures thereof, where $R_2$ is hydrogen or a functionalized $C_1$ to about a $C_{18}$ aliphatic carbon radical, linear or branched, and optionally containing sulfur, nitrogen, and/or oxygen or mixtures thereof.

11. The composition of claim 1 wherein said phosphite has the following generalized structure:

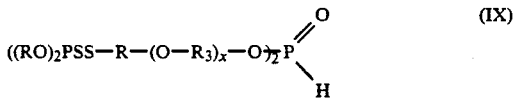

where R is a functionalized carbon radical of an aliphatic or aromatic moiety, substituted or unsubstituted, linear or branched and optionally containing sulfur, oxygen, and/or nitrogen or mixtures thereof, where $R_3$ is an aliphatic carbon radical of at least $C_2$ to about $C_{18}$.

12. The composition of claim 1 wherein said phosphite has the following generalized structure:

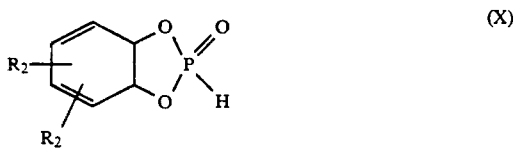

or open chain and/or oligomeric derivative thereof
where $R_2$ is hydrogen or a functionalized $C_1$ to about a $C_{18}$ aliphatic carbon radical, linear or branched, and optionally containing sulfur, nitrogen, and/or oxygen or mixtures thereof.

13. The composition of claim 1 wherein the molar ratio of olefinic oligomer to hydrogen phosphite varies from about 1:1 to about 1:2-10.

14. The composition of claim 1 wherein said oil of lubricating viscosity is selected from mineral oils, synthetic oils and mixtures thereof.

15. The composition of claim 14 wherein said oil is a mineral oil.

16. The composition of claim 14 wherein said oil is a synthetic oil.

17. The composition of claim 14 wherein said oil is a mixture of mineral oils and synthetic oils.

18. The composition of claim 1 wherein said composition is a grease composition prepared from mineral, synthetic or a mixture of mineral and synthetic oils.

19. The composition of claim 1 containing from about 0.001 to about 10 percent by weight of the total composition of said product of reaction.

20. The composition of claim 19 containing from about 0.1 to about 1% by weight of said product of reaction.

21. A lubricant composition comprising up to about 100% of a product of a reaction as described in claim 1.

22. A lubricant composition as described in claim 21 containing about 50 to 100% of said reaction product.

23. A lubricant composition containing about 10 to 90% of said product of a reaction described in claim 21.

24. A product of the reaction of a propylene based lube olefin oligomer and a functionalized phosphite selected from the group consisting of vicinal diol derived phosphites, sulfide containing vicinal derived phosphites, ether alcohol derived phosphites, amino alcohol derived phosphites, hydroxy-ester derived phosphites, heterocyclic substituted alcohol derived phosphites, alkoxylated amine derived phosphites, phosphorodithioate derived phosphites and aromatic derived phosphites or open chain and/or oligomeric derivatives thereof having a functionalized carbon radical of an aliphatic or aromatic moiety, substituted or unsubstituted, linear or branched and optionally containing sulfur, oxygen, and/or nitrogen or mixtures thereof wherein the reaction temperature varies from about 80° to 250° C. under ambient or slightly higher pressures or autogenous pressure and the molar ratio of propylene based lube olefinic oligomer to phosphite varies from less than molar, equimolar or more than molar amounts and wherein the propylene based lube oligomer has a kinematic viscosity at 100° C. of about 4 to 7 cs., and a VI in the range of 80 to 125, about 80 to 95% of which boils at about 700° F. and about 70% of said propylene based lube olefin has a BP $\geq$ 750° F.

25. The product of the reaction of claim 24 wherein the phosphite has the following generalized structure:

where R is a functionalized carbon radical of an aliphatic or aromatic moiety, substituted or unsubstituted, linear or branched and optionally containing sulfur, oxygen, and/or nitrogen or mixtures thereof.

26. The product of the reaction of claim 24 wherein the phosphite has the following generalized structure:

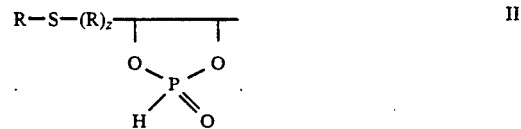

where R is a functionalized carbon radical of an aliphatic or aromatic moiety, substituted or unsubstituted, linear or branched and optionally containing sulfur, oxygen, and/or nitrogen or mixtures thereof and Z is 1.

27. The product of the reaction of claim 24 wherein the phosphite has the following generalized structure:

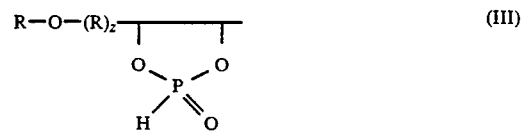

where R is a functionalized carbon radical of an aliphatic or aromatic moiety, substituted or unsubstituted, linear or branched and optionally containing sulfur, oxygen, and/or nitrogen or mixtures thereof,
where z is 1.

28. The product of the reaction of claim 24 wherein the phosphite has the following generalized structure:

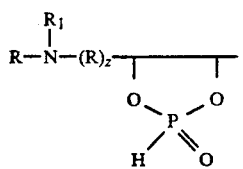

where R is a functionalized carbon radical of an aliphatic or aromatic moiety, substituted or unsubstituted, linear or branched and optionally containing sulfur, oxygen, and/or nitrogen or mixtures thereof, where $R_1$ is hydrogen or a functionalized $C_1$ to about a $C_{18}$ carbon radical of an aliphatic moiety, linear or branched, and optionally containing sulfur, nitrogen, and/or oxygen or mixtures thereof and where z is 1.

29. The product of the reaction of claim 24 wherein the phosphite has the following generalized structure:

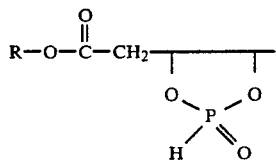

where R is a functionalized carbon radical of an aliphatic or aromatic moiety, substituted or unsubstituted, linear or branched and optionally containing sulfur, oxygen, and/or nitrogen or mixtures thereof.

30. The product of the reaction of claim 24 wherein the phosphite has the following generalized structure:

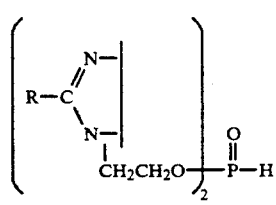

where R is a functionalized carbon radical of an aliphatic or aromatic moiety, substituted or unsubstituted, linear or branched and optionally containing sulfur, oxygen, and/or nitrogen or mixtures thereof.

31. The product of the reaction of claim 24 wherein the phosphite has the following generalized structure:

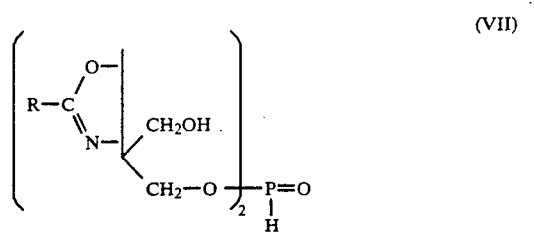

where R is a functionalized carbon radical of an aliphatic or aromatic moiety, substituted or unsubstituted, linear or branched and optionally containing sulfur, oxygen, and/or nitrogen or mixtures thereof.

32. The product of the reaction of claim 24 wherein the phosphite has the following generalized structure:

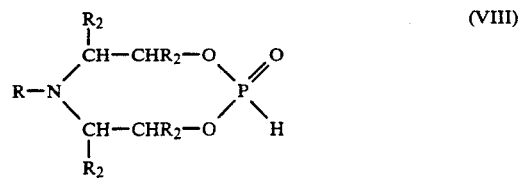

where R is a functionalized carbon radical of an aliphatic or aromatic moiety, substituted or unsubstituted, linear or branched and optionally containing sulfur, oxygen, and/or nitrogen or mixtures thereof.

33. The product of the reaction of claim 24 wherein the phosphite has the following generalized structure:

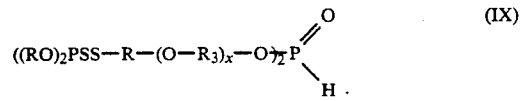

where R is a functionalized carbon radical of an aliphatic or aromatic moiety, substituted or unsubstituted, linear or branched and optionally containing sulfur, oxygen, and/or nitrogen or mixtures thereof, where $R_3$ is an aliphatic carbon radical of at least $C_2$ to about $C_{18}$.

34. The product of the reaction of claim 24 wherein the phosphite has the following generalized structure:

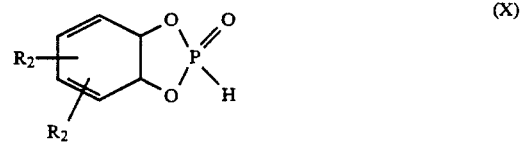

where $R_2$ is hydrogen or a functionalized $C_1$ to about a $C_{18}$ aliphatic carbon radical, linear or branched, and optionally containing sulfur, nitrogen, and/or oxygen or mixtures thereof.

* * * * *